(12) United States Patent
Falck-Pedersen

(10) Patent No.: US 6,599,737 B1
(45) Date of Patent: Jul. 29, 2003

(54) ADENOVIRAL VECTORS WITH TANDEM FIBER PROTEINS

(75) Inventor: Erik S. Falck-Pedersen, Dobbs Ferry, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 71 days.

(21) Appl. No.: 09/699,314

(22) Filed: Oct. 30, 2000

Related U.S. Application Data

(63) Continuation of application No. PCT/US99/09588, filed on Apr. 30, 1999
(60) Provisional application No. 60/083,572, filed on Apr. 30, 1998.

(51) Int. Cl.[7] ............. C12N 15/861; A61B 5/055; C12O 1/68; C12P 25/00; A01N 43/04
(52) U.S. Cl. ............. 435/320.1; 435/6; 435/69.1; 435/235.1; 435/325; 435/91.4; 435/91.41; 435/91.42; 435/456; 536/23.1; 536/24.1; 514/44; 424/93.2; 424/93.21
(58) Field of Search ............. 435/320.1, 235.1, 435/325.6, 456, 6, 69.1, 91.4; 424/199.1, 233.1, 93.2, 93.21, 9; 536/23.1, 24.1, 23.4; 514/44

(56) References Cited

U.S. PATENT DOCUMENTS

| | | |
|---|---|---|
| 4,578,079 A | 3/1986 | Ruoslahti et al. |
| 4,593,002 A | 6/1986 | Dulbecco |
| 4,792,525 A | 12/1988 | Ruoslahti et al. |
| 5,166,320 A | 11/1992 | Wu et al. |
| 5,223,409 A | 6/1993 | Ladner et al. |
| 5,403,484 A | 4/1995 | Ladner et al. |
| 5,443,953 A | 8/1995 | Hansen et al. |
| 5,521,291 A | 5/1996 | Curiel et al. |
| 5,543,328 A * | 8/1996 | McClelland et al. |
| 5,547,932 A | 8/1996 | Curiel et al. |
| 5,559,099 A | 9/1996 | Wickham et al. |
| 5,571,698 A | 11/1996 | Ladner et al. |
| 5,622,699 A | 4/1997 | Ruoslahti et al. |
| 5,663,143 A | 9/1997 | Ley et al. |
| 5,693,509 A | 12/1997 | Cotten et al. |
| 5,695,991 A | 12/1997 | Lindholm et al. |
| 5,712,136 A | 1/1998 | Wickham et al. |
| 5,731,190 A | 3/1998 | Wickham et al. |
| 5,756,086 A | 5/1998 | McClelland et al. |
| 5,770,442 A | 6/1998 | Wickham et al. |
| 5,837,500 A | 11/1998 | Ladner et al. |
| 5,837,511 A * | 11/1998 | Falck-Pedersen et al. |
| 5,871,727 A | 2/1999 | Curiel |
| 5,885,808 A | 3/1999 | Spooner et al. |
| 5,922,315 A | 7/1999 | Roy |
| 5,981,273 A | 11/1999 | Curiel et al. |

FOREIGN PATENT DOCUMENTS

| | | |
|---|---|---|
| EP | 0 959 135 A1 | 11/1999 |
| WO | WO 93/07282 A | 4/1993 |
| WO | WO 93/07283 A | 4/1993 |
| WO | WO 94/10323 A | 5/1994 |
| WO | WO 94/15644 A | 7/1994 |
| WO | WO 94/17832 A | 8/1994 |
| WO | WO 94/24299 A | 10/1994 |
| WO | WO 95/05201 A1 | 2/1995 |
| WO | WO 95/26412 A | 10/1995 |
| WO | WO 95/31566 A | 11/1995 |
| WO | WO 96/07734 A | 3/1996 |
| WO | WO 96/13597 A2 | 5/1996 |
| WO | WO 96/26281 A1 | 8/1996 |
| WO | WO 97/38723 A1 | 10/1997 |
| WO | WO 98/07865 A | 2/1998 |
| WO | WO 98/13499 A | 4/1998 |
| WO | WO 98/22609 A | 5/1998 |
| WO | WO 98/32842 A | 7/1998 |
| WO | WO 98/33929 A | 8/1998 |
| WO | WO 98/39464 A | 9/1998 |
| WO | WO 98/44121 A | 10/1998 |
| WO | WO 98/51788 A | 11/1998 |
| WO | WO 98/500583 A1 | 11/1998 |
| WO | WO 99/36545 A2 | 7/1999 |
| WO | WO 99/41359 A | 8/1999 |

OTHER PUBLICATIONS

Michael et al., *Gene Therapy*, 2 (9), 660–668 (Nov. 1995).
Albiges–Rizo et al., *J. Biol. Chem.*, 266 (6), 3961–3967 (Feb. 1991).
Bai et al., *J. Virol.*, 67 (9), 5198–5205 (Sep. 1993).
Bergelson et al., *J. Virol.*, 72 (1), 415–419 (Jan. 1998).
Crawford–Miksza et al., *J. Virol.*, 70 (3), 1836–1844 (Mar. 1996).
Crompton et al., *J. Gen. Virol.*, 75 (1), 133–139 (Jan. 1994).
Foreman et al., *Hum. Gene Ther.*, 9, 1313–1321 (Jun. 1998).
Gall et al., *J. Virol.*, 70 (4), 2116–2123 (Apr. 1996).
Hong et al., *Virology*, 185 (2), 758–767 (Dec. 1991).
Karayan et al., *Virology*, 202 (2), 782–785 (Aug. 1994).
Kleiboeker, *Virus Research*, 39 (2–3), 299–309 (Dec. 1995).
Kovesdi et al., *Curr. Opin. Biotechnol.*, 8 (5), 583–589 (Oct. 1997).
Krasnykh et al., *J. Virol.*, 70 (10), 6839–6846 (Oct. 1996).
Mastrangeli et al., *Hum. Gene Ther.*, 7, 79–87 (Jan. 1996).
Mathias et al., *J. Virol.*, 68 (10), 6811–6814 (Oct. 1994).
Michael et al., presented at *Adenovirus Workshop: St. Andrews University*, p. 52 (Jul. 13–15, 1995).
Nemerow et al., *Trends in Cell Biology*, 4, 52–55 (Feb. 1994).

(List continued on next page.)

*Primary Examiner*—David Guzo
*Assistant Examiner*—Maria Marvich
(74) *Attorney, Agent, or Firm*—Leydig, Voit & Mayer, Ltd.

(57) ABSTRACT

The present invention provides an adenoviral gene transfer vector comprising a first fiber gene and a second fiber gene, wherein the fiber genes are different. The present invention also provides related recombinant adenoviral gene transfer vectors and methods of propagating an adenovirus with a fiber protein that does not bind to a native adenoviral fiber receptor.

24 Claims, No Drawings

OTHER PUBLICATIONS

Novelli et al., *Virology*, 185 (1), 365–376 (Nov. 1991).
Roelvink et al., *J. Virol.*, 70 (11), 7614–7621 (Nov. 1996).
Roelvink et al., *J. Virol.*, 72 (10), 7909–7915 (Oct. 1998).
Signas et al., *J. Virol.*, 53 (2), 672–678 (Feb. 1985).
Wickham et al., *Cell*, 73, 309–319 (Apr. 1993).
Wickham et al., *J. Cell Biol.*, 127 (1), 257–264 (Oct. 1994).
Wickham et al., *Biotechnol. Prog.*, 11 (2), 164–170 (Mar.–Apr. 1995).
Wickham et al., *Gene Therapy*, 2 (10), 750–756 (Dec. 1995).
Wickham et al., *J. Virol.*, 70 (10), 6831–6838 (Oct. 1996).
Wickham et al., *Nature Biotechnol.*, 14, 1570–1573 (Nov. 1996).
Wickham et al., *Nature Biotechnol.*, 15, 717 (Aug. 1997).
Wickham et al., *J. Virol.*, 71 (10), 7663–7669 (Oct. 1997).
Wickham et al., *J. Virol.*, 71 (11), 8221–8229 (Nov. 1997).
Wickham et al., *Cancer Immunol. Immunother.*, 45 (3–4), 149–151 (Nov.–Dec. 1997).

* cited by examiner

ADENOVIRAL VECTORS WITH TANDEM FIBER PROTEINS

CROSS-REFERENCE TO RELATED PATENT APPLICATIONS

This patent application is a continuation of International Patent Application No. PCT/US99/09588, filed Apr. 30, 1999, which designates the U.S., claiming priority to U.S. Patent Application No. 60/083,572, filed Apr. 30, 1998.

STATEMENT AS TO RIGHTS TO INVENTIONS MADE UNDER FEDERALLY SPONSORED RESEARCH AND DEVELOPMENT

This invention was made with Government support under Grant Number PO1 HL57146 awarded by the National Institutes of Health. The United States Government may have certain rights in this invention.

TECHNICAL FIELD OF THE INVENTION

The present invention relates to adenoviral gene transfer vectors, as well as methods of making and using the same.

BACKGROUND OF THE INVENTION

The 49 serotypes of human adenovirus are divided into six serogroups, A–F. All human adenoviruses have a capsid that contains 12 fiber proteins and other capsid proteins, such as penton base protein and hexon protein. The 12 fiber proteins extend from the surface of the capsid protein and bind with a native receptor that is expressed on the surface of cells that adenoviruses efficiently infect. This initial binding step is usually followed by a second virus-host cell interaction in which the penton base protein binds to an integrin. The binding of penton base protein to the cell is necessary for integrin mediated endocytosis of the virus. However, it is the binding characteristics of the fiber protein that are normally dominant (e.g., in non-recombinant adenoviruses) in selecting which cell types are infected by an adenovirus.

Of the 49 different serotypes of human adenoviruses, the subgroup F viruses (Ad40 and Ad41) are unique. They are the only serotypes that contain two distinct fiber genes (one short and one long) in the major late transcription unit. Both of these fiber genes are expressed and form homotrimers in equimolar ratios on the surface of group F adenoviruses. However, group F viruses are extremely fastidious (i.e., have complex requirements for viral propagation), and, in general, do not grow well in cell types normally used to grow adenoviruses, such as A549 cells, HeLa cells, and HEK-293 cells. For these and other reasons, it has not been desirable to use group F adenoviruses to make adenoviral vectors that comprise and direct the expression (in target cells) of heterologous genes (i.e., as gene transfer vectors).

In contrast to the group F adenoviruses, Ad2 (group C), Ad5 (group C), and some other adenoviruses have been well studied and are among the serotypes that are commonly adapted to gene transfer methods. Such adenoviral gene transfer vectors have been successfully employed as vehicles to transfer therapeutic, immunogenic or prophylactic, and experimental genes to mammals in vivo, as vehicles to transfer genes to cells and tissues in vitro (including for subsequent ex vivo therapies or studies), as models of regulated eukaryotic transcription, and for other purposes. Adenoviral vectors are among the preferred contemporary gene transfer vectors employed, because adenoviral vectors have relatively low toxicity to host cells, efficiently infect a broad range of host cells, do not typically integrate into the host cell genome, and have a substantial number of other advantages.

There are, however, a substantial number of cell types that adenoviral vectors do not efficiently infect. Moreover, for some applications, there has been a desire in the art to limit the host cell range of adenoviral vectors. Accordingly, there has been a significant effort to make chimeric adenoviral vectors having modified coat proteins which change and control the efficiency with which adenoviral vectors infect host cells in vivo and in vitro (see, e.g., U.S. Pat. No. 4,593,002 (Dulbecco), U.S. Pat. No. 5,521,291 (Curiel et al.), U.S. Pat. No. 5,543,328 (McClelland et al.), U.S. Pat. No. 5,547,932 (Curiel et al.), U.S. Pat. No. 5,559,099 (Wickham et al.), U.S. Pat. No. 5,695,991 (Lindholm et al.), U.S. Pat. No. 5,712,136 (Wickham et al.), and International Patent Application WO 94/10323 (Spooner et al.)). These modified coat proteins bind or selectively bind to a protein on the surface of a cell, which mediates the uptake of the receptor. However, many of these chimeric coat proteins substantially reduce the infection efficiency into preferred production cell lines (e.g., HEK-293 cells). The result of this decreased infection efficiency (in preferred production cell lines) can include lower yields and titers, the need to produce novel cell lines to support propagation of the novel vectors, and other deleterious effects.

In view of the foregoing, there exists a need for an adenoviral gene transfer vector or a method for producing an adenoviral vector that has a novel target cell range and/or allows the desired control of vector tropism, and which also allows easy and efficient vector production. The present invention provides such a vector and method. These and other advantages of the present invention, as well as additional inventive features, will be apparent from the description of the invention provided herein.

BRIEF SUMMARY OF THE INVENTION

The present invention provides an adenoviral gene transfer vector comprising a passenger gene and two types of fiber genes as well as the genome of the present inventive gene transfer vector. Optionally, one type of the fiber proteins of the adenoviral gene transfer vector has affinity with a natural adenoviral receptor, while the other type of fiber does has affinity for a novel cell surface binding site, but does not have affinity for a natural adenoviral receptor. Advantageously, the ratio of the types of fiber proteins on the adenoviral gene transfer vector can be manipulated to impart selectivity of binding to cells in vivo for research or other uses. The present invention also provides a chimeric adenoviral fiber gene that encodes a fiber protein that has a Factor Xa cleavage site.

DETAILED DESCRIPTION OF THE INVENTION

While applicants do not wish to be bound to any particular theory, it is believed that the adenoviral fiber protein is dominant in determining which types of cells will be efficiently infected when contacted with an adenovirus. Accordingly, recombinant fiber proteins have been made which have affinity for cellular receptors other than the native adenoviral fiber receptor (hereinafter referred to as CAR, which stands for Coxsackievirus-Adenovirus Receptor; see Bergelson et al., *Science*, 275, 1320–1323 (1997), and Hong et al., *EMBO J.*, 16, 2294–2306 (1997)). In many embodiments of these chimeric adenoviral fiber proteins, the binding moiety of the native fiber protein is destroyed, deleted, or sterically obscured. Therefore, adenoviruses comprising the chimeric adenoviral fiber protein must be propagated in specialized cells expressing or overexpressing a receptor for the chimeric fiber protein. Several embodiments of the present invention provide a novel adenovirus comprising, and directing the expression of (in a target cell), a heterologous gene of interest (i.e., a gene transfer vector) and a convenient method of obviating this and other problems.

One embodiment of the present inventive method comprises making and using the present inventive adenovirus to facilitate propagation of an adenoviral vector that has a chimeric fiber protein that does not bind to CAR. The present inventive adenovirus is an adenovirus having two types of fiber proteins, at least one of which does not efficiently bind to CAR. The second type of fiber gene can be a wildtype fiber protein or is a chimeric fiber protein that retains the ability to bind to CAR. Thus, the inventive adenovirus can have one type of fiber protein with the ability to bind to CAR (or another receptor present on the surface of a preferred production cell line for propagating a particular virus) and a second type of fiber protein that binds to a receptor present on the surface of a target cell of interest.

Effective adenoviral infection does not require more than one or a few fiber proteins that have the capacity to bind to a cell surface receptor for the fiber protein. Therefore, the second type of fiber gene efficiently mediates the uptake of the virus by production cells, despite the fact that not all twelve fiber proteins—and perhaps only one fiber protein per capsid—have affinity for the production cell; especially when the production cell is maintained in vitro, where it is possible to obtain high viral particle to cell ratios. The present invention is especially useful where it is difficult to make or maintain the production cell (e.g., cells expressing an essential gene function of both the E1 and the E4 regions of the adenoviral genome or other cytotoxic proteins).

In another embodiment of the present invention, the first fiber protein is chimeric or otherwise does not have affinity with CAR. The chimeric or non-CAR binding fiber protein (in some embodiments both types of fiber protein) comprises a nonnative amino acid sequence in place of or in addition to the native amino acid sequence of the fiber protein. The nonnative amino acid can be placed in an exposed loop of the fiber protein, at the C-terminus of the fiber protein, and/or can replace discreet sections of the fiber protein, such as the knob. The nonnative amino acid comprises sequences with suitable affinity with a cell surface receptor (naturally occurring or induced). Additionally, the nonnative amino acid can comprise sequences that mediate optimal interaction of the fiber protein with the targeted receptor such as spacer sequences. Such fiber proteins are now well known in the art, and specific teachings describing how to make and use these fiber proteins can be found in U.S. Pat. No. 4,593,002 (Dulbecco), U.S. Pat. No. 5,521,291 (Curiel et al.), U.S. Pat. No. 5,543,328 (McClelland et al.), U.S. Pat. No. 5,547,932 (Curiel et al.), U.S. Pat. No. 5,559,099 (Wickham et al.), U.S. Pat. No. 5,695,991 (Lindholm et al.), U.S. Pat. No. 5,712,136 (Wickham et al.), published International Patent Applications WO 94/10323 (Spooner et al.), WO 98/44121 (LeGrand et al.), and WO 98/54346 (Wickham et al.), and in other sources.

The two types of fiber genes can also be obtained or derived from adenoviruses belonging to different serogroups. For example, the fiber protein encoded by one type of fiber gene can be of a serotype that efficiently binds to CAR (e.g., Ad2 or Ad5) and the other can be from subgroup B (e.g., Ad3), which does not bind to CAR. Optionally, the vector from which the fiber gene (or derivative thereof) is obtained can be a group C vector that can also comprises a fiber gene from a group F adenovirus (e.g., Ad40 or Ad41). At least because group F adenoviruses are fastidious, it is preferable in some embodiments for the adenovirus to be of a serogroup other than group F. Group F adenoviruses are most commonly defined by being neutralized by antibodies that bind to the coat of Ad40 or Ad41 (a neutralized virus cannot efficiently infect a cell) wherein the antibody or anti-sera containing the anti-body does not neutralize adenoviruses of non-group F adenoviruses. However, for the purposes of the present invention, group F adenoviruses can also be defined by the E1 sequences, E2 sequences, and the E4 sequences, which contain essential gene functions that are not efficiently complemented by corresponding group C genes (except when replaced entirely as in an adenoviral amplicon or "gutless" vector).

The Ad7 fiber is less effective than group C fibers (e.g., Ad2 fiber or Ad5 fiber) at infecting CAR-expressing cells in vivo, but is capable of efficiently mediating the infection of CAR-expressing cells in vitro. An adenovirus having two types of fiber protein, one specific for a selected cell type and the other being an Ad7 fiber, would be more selective for the targeted cells than if the Ad5 fiber replaced the Ad7 fiber. Accordingly, for many embodiments of the present invention, the Ad7 fiber gene is a preferred type of second fiber gene.

It will be appreciated that any embodiment of the present inventive adenovirus or adenoviral genomes can also comprise a passenger gene. Passenger genes can be any suitable DNA that is of interest in any suitable field, including but not limited to experimental biology, protein or bio-product production, and medicine (e.g., therapeutic, diagnostic, and prophylactic genes).

The fiber proteins present on the present inventive adenovirus are preferably encoded in cis (i.e., by the adenoviral genome), but may be encoded in trans. At least one fiber gene is preferably encoded by the L5 transcript of the major late transcription unit of the adenoviral genome (e.g., in the natural location of the fiber gene). However, the fiber genes can be placed at any suitable location within the genome (e.g., in the E1 or E3 regions of the adenoviral genome). Additionally, either or both fiber genes can be placed under the control of a regulable promoter. If a regulable promoter is used, it is ideally induced or repressed by changing the production cell environment (e.g., changing temperature or adding an inducer or repressor to the medium). The use of inducible and repressible promoters (i.e., regulable promoters) is within the skill of the ordinary artisan.

In an especially preferred embodiment, both fiber genes are placed in tandem in the L5 region of the adenoviral vector. For example, a second fiber gene can be inserted into an adenoviral vector either upstream of the ATG of the first fiber gene or downstream of the polyadenylation of the second fiber gene. The added fiber gene carries with it (or otherwise is provided with) independent splice acceptor elements and polyadenylation signals. This embodiment provides several substantial advantages. First, the fiber genes are temporally regulated by the normal adenoviral regulation of the major late transcription unit and are commonly induced to express fiber protein at the high levels required for efficient adenoviral packaging. Second, one fiber gene will be proximal to, and the other fiber gene will be distal from, the site of transcription initiation. Unless additional elements are added to the vector, the ratio of proximal fiber protein to distal fiber protein produced is from about 3:1 to about 11:1, and preferably about 6:1 to about 10:1, and most preferably about 8:1. Accordingly, the proximal fiber protein is over-represented on the adenoviral capsid so that statistically about 8 to 11 proximal fiber proteins and about 4 to 1 distal fiber proteins are present on the capsid. Since in vitro infection is usually much more efficient than in vivo infection, only one fiber protein need be present on the capsid to effect efficient uptake into the production cell. Advantageously, this leaves up to 11 of the 12 possible fiber proteins to direct in vivo targeting of the recombinant adenoviral vector.

Any suitable technique can be used to make the present inventive adenoviral vectors and recombinant adenoviruses. When inserting an additional gene into the L5 region of the adenoviral genome, insertions are preferably made in the 3' of the L5 poly(A) site in an area that does not perturb the E4 transcript or reading frame which is expressed on the opposite strand of the genome downstream from the fiber region. Inserted fiber genes can also carry their own 5' and 3' RNA processing elements of the major late transcription unit L5 exon. Gall et al., *Virology*, 70, 2116–2123 (1996), discloses suitable molecular biology techniques which can be used to make the present invention.

The present invention also provides a fiber protein that can trimerize and can be efficiently incorporated into functional adenoviral capsids and which comprises a site that can be efficiently cut by a protease. Preferably, the protease recognition site is inserted into an exposed loop of the fiber gene, and most preferably, the recognition site is inserted into the AB loop of the fiber protein. Factor Xa protease is preferred as it is available at favorable costs, recognizes a site sufficiently small to be inserted into the fiber gene without disrupting essential secondary or higher order structures of the fiber protein; however, the enzyme does not effectively cleave wildtype adenoviral coat proteins (at least in essential regions), and effectively cuts heterologous Factor Xa recognition sites inserted into chimeric fiber genes. Factor Xa is a serine endopeptidase that hydrolyzes peptide bonds at the carboxylic side of Arg within the sequence -Ile-Glu-Gly-Arg-X- (SEQ ID NO: 1). Factor Xa is well known in the art and is available from commercial suppliers such as Boehringer Mannheim and Hoffman-La Roche.

In one embodiment of the present invention, the protease recognition site is incorporated into a first fiber protein specific for a receptor on a production cell of an adenovirus having a second fiber protein. Therefore, the adenovirus of this embodiment can be propagated in the production cell until it is harvested for use. Prior to use, the adenovirus is incubated in the presence of the protease which cleaves the cell targeting moiety of the first fiber protein from the adenoviral capsid. The proteolytically processed adenovirus can then be introduced into a mixed population of cells (in vivo or in vitro), wherein the adenovirus will efficiently infect only those cells that have a receptor specific for the second fiber protein. This embodiment is particularly useful in the identification of ligands for novel cell populations, because no special cells are required to propagate a library of adenoviruses comprising (i) the CAR-specific fiber protein having a protease recognition site and (ii) a novel chimeric fiber protein comprising a particular or random nonnative amino acid sequence. Variations of this process are referred to as "panning" of "bio-panning". It is within the skill of the ordinary artisan to conduct such panning experiments.

In another embodiment, the fiber protein containing a protease recognition site has at least 60%, and preferably at least 90%, identity to a wild type group C fiber protein.

The following example further illustrates the present invention but, of course, should not be construed as in any way limiting its scope.

EXAMPLE

This example illustrates the construction of three embodiments of the present inventive tandem fiber adenovirus. It will be appreciated that other embodiments can be constructed using similar or other techniques, that are within the skill of the ordinary artisan.

pAd70-100 is a plasmid comprising wild-type Ad5 sequence from map unit 70 to map unit 100. pAd70-100 was converted to pAd70-100d1E3 by deleting the majority of the E3 transcription unit.

The deletion of the E3 region was accomplished as follows. pAd70-100 was partially restriction digested with the restriction enzyme Mun I followed by insertion of a linker having a Mun I and Bam HI site. The insertion of the linker allowed the selection of pAd70-100+BamHI, by screening for clones with a Bam HI site only at 91 map units. E3 sequences from 78.6 to 85.9 map units were deleted and a unique Pac I site was inserted by PCR amplification of DNA from map units 76.2 to 78.6 (hereinafter "fragment 1") and 85.9 to 87 (hereinafter "fragment 2"). Pac I sites were present at the 78.6 and 85.9 ends of fragments 1 and 2, respectively. Fragment 1 was digested with Srf I and Pac I, fragment 2 was digested with Pac I and Sph I, and pAd70-100+BamHI with Srf I and Sph I. Ligation of the three fragments yielded the plasmid pAd70-100d1E3. Multiple right-end genomes were created from pAd70-100d1E3.- pAd70-100d1E3 was used to generate a right-end adenoviral genome comprising the Ad7a fiber gene in addition to the Ad5 fiber gene. A linker containing a Pac I site was inserted into pAd70-100d1E3 at the unique Bam HI site to generate pAd70-100d1E3Pac$_{Bam}$. The fiber gene from Ad7 was obtained by Pac I (to Pac I) restriction digest and ligated into the Pac I site of pAd70-100d1E3Pac$_{Bam}$.

pAd70-100d1E3 was also used to generate pAd70-100d1E3.Fiber7. To do this, the Ad7 fiber gene was PCR amplified from Ad7 a viral DNA so as to insert Pac I and Bam HI restriction enzyme sites upstream and downstream of the fiber coding sequence. The placement of the Pac I site in pAd70-100d1E3 allows use of the normal splice acceptor of the Ad7 fiber mRNA, which overlaps with the translation initiation codon. The 3' boundary of the PCR product is outside (downstream on the R strand) of the coding region of the L5 poly(A) signal sequence, in an area that does not perturb the E4 transcript or open reading frame (which is expressed from the opposite strand of the genome downstream of the fiber region). The termination codon for fiber is integrated into the L5 poly(A) signal. Therefore, the Ad7 PCR product included both the 5' and 3' RNA processing elements of the major late transcription unit L5 exon, as well as the complete coding sequence of the fiber gene.

A PCR product of the expected size (1083 base pairs) was ligated into pAd70-100d1E3 at the unique Pac I and Bam HI restriction sited to generate pAd70-100d1E3.Fiber7. Using similar techniques, the short and long fiber genes of Ad41 were ligated into pAd70-100d1E3.Fiber7 to generate pAd70-100d1E3.Fiber7/Fiber41$_{short}$ and pAd70-100d1E3.Fiber7/Fiber41$_{long}$, respectively.

Each of the three right-end adenoviral genomes were co-transfected into 293 cells with left-end adenoviral arms (some of which included deletions of the E1 region, and some of which included passenger genes in either the E1 region or the deleted E3 region) to generate adenoviral genomes encoding more than one fiber (i.e., Ad5-Ad7, Ad5-Ad41$_{long}$, and Ad5-Ad41$_{short}$). The resultant viruses had tandem fiber capsids.

All of the references cited herein, including patents, patent applications, and publications, are hereby specifically incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. An adenoviral gene transfer vector comprising a genome comprising a first fiber gene and a second fiber gene, wherein the first fiber gene and the second fiber gene are different, and wherein the adenoviral gene transfer vector is not a serotype F adenovirus.

2. The adenoviral gene transfer vector of claim 1, wherein at least the first fiber gene is chimeric.

3. The adenoviral gene transfer vector of claim 1, wherein the first fiber gene comprises a nonnative amino acid sequence in place of or in addition to a native amino acid sequence.

4. The adenoviral gene transfer vector of claim 1, wherein the genome of the vector is a group C genome modified by insertion of at least one fiber gene of an adenovirus selected from the group consisting of Ad40 and Ad41.

5. The adenoviral gene transfer vector of claim 1, wherein the first fiber gene is in the L5 region of the adenoviral genome and the second fiber gene is in the L5 region of the adenoviral genome.

6. The adenoviral gene transfer vector of claim 1, wherein the first and the second fiber genes are transcribed as part of the major late transcription unit.

7. The adenoviral gene transfer vector of claim 1, wherein the second fiber gene is specific for a native adenoviral fiber receptor.

8. The genome of the adenoviral gene transfer vector of claim 1.

9. The adenoviral gene transfer vector of claim 1, wherein the adenoviral gene transfer vector further comprises a passenger gene.

10. A recombinant adenovirus comprising a first fiber protein and a second fiber protein, wherein the first fiber protein and the second fiber protein are different, and wherein the recombinant adenovirus is not a serotype F adenovirus.

11. The recombinant adenovirus of claim 10, wherein the fist fiber protein is chimeric.

12. The recombinant adenovirus of claim 10, wherein the recombinant adenovirus comprises 8 to 11 copies of the first fiber protein.

13. The recombinant adenovirus of claim 11, wherein the recombinant adenovirus comprises 8 to 11 chimeric fiber proteins.

14. An adenoviral gene transfer vector comprising a genome comprising a first fiber gene, and a second fiber gene, wherein the first fiber gene and the second fiber gene are obtained from adenoviruses belonging to different serogroups.

15. The adenoviral gene transfer vector of claim 14, wherein at least the first fiber gene is chimeric.

16. The adenoviral gene transfer vector of claim 14, wherein the genome of the adenoviral gene transfer vector is a group C adenoviral genome modified by insertion of at least one fiber gene of an adenovirus selected from the group consisting of Ad40 and Ad41.

17. The adenoviral gene transfer vector of claim 14, wherein the first fiber gene is in the L5 region of the adenoviral genome, and the second fiber gene is in the L5 region of the adenoviral genome.

18. The adenoviral gene transfer vector of claim 14, wherein the first fiber gene and the second fiber gene are transcribed as part of the major late transcription unit.

19. The genome of the adenoviral gene transfer vector of claim 14.

20. The adenoviral gene transfer vector of claim 14, wherein the adenoviral gene transfer vector further comprises a passenger gene.

21. A recombinant adenovirus comprising a fist fiber protein and a second fiber protein, wherein the first fiber protein and the second fiber protein are obtained from adenoviruses belonging to different serogroups.

22. The recombinant adenovirus of claim 21, wherein the first fiber protein is chimeric.

23. The recombinant adenovirus of claim 21, wherein the recombinant adenovirus comprises 8 to 11 copies of the first fiber protein.

24. The recombinant adenovirus of claim 22, wherein the recombinant adenovirus comprises 8 to 11 chimeric fiber proteins.

\* \* \* \* \*

SEQUENCE LISTING

```
<160> NUMBER OF SEQ ID NOS: 1

<210> SEQ ID NO 1
<211> LENGTH: 5
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: "Xaa" may be any amino acid

<400> SEQUENCE: 1

Ile Glu Gly Arg Xaa
1               5
```